US009417356B2

(12) United States Patent
Chen et al.

(10) Patent No.: US 9,417,356 B2
(45) Date of Patent: Aug. 16, 2016

(54) MILLIMETER WAVE HOLOGRAPHIC SCAN IMAGING APPARATUS FOR HUMAN BODY SECURITY INSPECTION

(71) Applicant: Nuctech Company Limited, Haidian District, Beijing (CN)

(72) Inventors: Zhiqiang Chen, Beijing (CN); Yuanjing Li, Beijing (CN); Ziran Zhao, Beijing (CN); Wanlong Wu, Beijing (CN); Xilei Luo, Beijing (CN); Yinong Liu, Beijing (CN); Li Zhang, Beijing (CN); Bin Sang, Beijing (CN); Zongjun Shen, Beijing (CN); Yingkang Jin, Beijing (CN); Zhimin Zheng, Beijing (CN)

(73) Assignee: Nuctech Company Limited, Haidian District, Beijing (CN)

( * ) Notice: Subject to any disclaimer, the term of this patent is extended or adjusted under 35 U.S.C. 154(b) by 0 days.

(21) Appl. No.: 14/247,837

(22) Filed: Apr. 8, 2014

(65) Prior Publication Data
US 2015/0048251 A1 Feb. 19, 2015

(30) Foreign Application Priority Data

Aug. 15, 2013 (CN) .......................... 2013 1 0356863

(51) Int. Cl.
*G01V 8/20* (2006.01)
*G01V 8/26* (2006.01)
(Continued)

(52) U.S. Cl.
CPC *G01V 8/20* (2013.01); *G01N 22/00* (2013.01); *G01V 8/005* (2013.01); *G01V 8/26* (2013.01)

(58) Field of Classification Search
CPC .................................. G01V 8/20; G01V 8/26
See application file for complete search history.

(56) References Cited

U.S. PATENT DOCUMENTS 5,455,590 A 10/1995 Collins et al.
7,405,692 B2 * 7/2008 McMakin et al. .............. 342/22
(Continued)

FOREIGN PATENT DOCUMENTS

CN 1586400 A 3/2005
CN 101482523 A 7/2009
(Continued)

OTHER PUBLICATIONS

International Search Report and Written Opinion of the International Searching Authority (English translation) for corresponding International Patent Application No. PCT/CN2014/070597 mailed Jun. 9, 2014.
(Continued)

*Primary Examiner* — David Porta
*Assistant Examiner* — Faye Boosalis
(74) *Attorney, Agent, or Firm* — Merchant & Gould P.C.

(57) ABSTRACT

The present invention discloses a millimeter wave holographic scan imaging apparatus for inspecting a human body. The apparatus includes a first millimeter wave transceiver device (40) comprising a first millimeter wave transceiver antenna array (41) for transmitting and receiving a first millimeter wave signal; a second millimeter wave transceiver device (40'), which comprises a second millimeter wave transceiver antenna array (41') for transmitting and receiving a second millimeter wave signal, and is configured in opposite direction with relation to the first millimeter wave transceiver device; a connection member (26, 27) for connecting the first millimeter wave transceiver device (40) to the second millimeter wave transceiver device (40'); and a drive device (50), which drives one of the first and the second millimeter wave transceiver devices such that the first millimeter wave transceiver device (40) and the second millimeter wave transceiver device (40') move in opposite directions.

15 Claims, 9 Drawing Sheets

(51) Int. Cl.
*G01V 8/00* (2006.01)
*G01N 22/00* (2006.01)

(56) References Cited

U.S. PATENT DOCUMENTS

| | | | |
|---|---|---|---|
| 7,844,081 B2 * | 11/2010 | McMakin et al. | 382/115 |
| 2005/0232459 A1 * | 10/2005 | Rowe | G01S 13/86 382/100 |
| 2011/0163231 A1 | 7/2011 | Salmon | |

FOREIGN PATENT DOCUMENTS

| | | |
|---|---|---|
| CN | 101806755 A | 8/2010 |
| CN | 202013428 U | 10/2011 |
| CN | 102393536 A | 3/2012 |
| CN | 102393537 A | 3/2012 |
| CN | 102426361 A | 4/2012 |
| CN | 102508240 A | 6/2012 |
| CN | 102508306 A | 6/2012 |
| CN | 103197353 A | 7/2013 |
| CN | 103267978 A | 8/2013 |
| CN | 203385855 U | 1/2014 |
| CN | 203385856 U | 1/2014 |
| CN | 203385857 U | 1/2014 |
| CN | 203433126 U | 2/2014 |
| JP | H01-121707 A | 5/1989 |
| JP | 11-035246 A | 2/1999 |
| JP | 2007-532907 A | 11/2007 |
| JP | 2011-505565 A | 2/2011 |
| JP | 2015-036679 A | 2/2015 |
| RU | 2 367 976 C2 | 6/2009 |
| WO | WO 2005/004053 A2 | 1/2005 |
| WO | WO 2010/032003 A1 | 3/2010 |

OTHER PUBLICATIONS

Russian Office Action for corresponding application RU 2014119429 mailed Jul. 1, 2015, English translation.
Japanese Office Action for corresponding application JP 2014-092628 mailed Jul. 28, 2015.
United Kingdom Search and Examination Report for corresponding application GB1407499.1 mailed Oct. 16, 2014.
Japanese Office Action for corresponding application JP 2014-092628 mailed Jun. 10, 2014.
Japanese Office Action for corresponding Japanese Patent Application No. 2014-092628 mailed Feb. 23, 2016.

* cited by examiner

MILLIMETER WAVE HOLOGRAPHIC SCAN IMAGING APPARATUS FOR HUMAN BODY SECURITY INSPECTION

CROSS-REFERENCE TO RELATED APPLICATION

This application claims the benefit of Chinese Patent Application No. 201310356863.8 filed on Aug. 15, 2013 in the State Intellectual Property Office of China, and which application(s) are incorporated herein by reference. To the extent appropriate, a claim of priority is made to each of the above disclosed applications.

BACKGROUND OF THE INVENTION

1. Field of the Invention

The present invention relates to an inspection apparatus for human body security inspection, in particular, to a millimeter wave holographic scan imaging apparatus for human body security inspection.

2. Description of the Related Art

The known security inspection apparatus mainly includes a metal detector, a trace detector and a X-ray transmission apparatus. Specifically, a metal detector exhibits sensitivity only on metal material. A trace detector may only detect explosive substance and drugs. A X-ray transmission apparatus may be used to detect material including metal/non-metal article, explosive substance and drugs etc., and possess a relative high spatial resolution and process in a certain scanning speed. However, due to harm to human body from X-ray photoionizing radiation, a X-ray transmission apparatus is limited on security inspection of human body.

With comparison to the conventional human body inspection system, a millimeter wave inspection imaging technology possesses advantages of penetrating clothing of human body, emitting radiation in small dose to human body, identifying various types of metal and nonmetal contraband articles. With rapid development in millimeter wave technologies and reduction of the cost of millimeter wave devices, millimeter wave inspection apparatus has become more and more popular and plays a more important role in human body security inspection.

The millimeter wave inspection imaging technology can be characterized into two types: passive millimeter wave inspection imaging technology and active millimeter wave inspection imaging technology, wherein the active millimeter wave inspection imaging technology mainly pertains to holographic scan imaging technology.

With regard to active millimeter wave three dimensional holographic scan imaging technology applied to human body security inspection, a cylinder scanning imaging technology is widely used. However, the cylinder scanning imaging technology results in a bulky volume of the apparatus and complicated calculation. Further, the data is theoretically obtained through approximation and accordingly imaging accuracy cannot be ensured. In addition, the cylinder scanning process is performed with vertical antenna arrays, in which the antenna array has a relative big length and rather excessive units, and thus resulting in higher costs. Further, due to its complexity and bigger occupying floor area, the cylinder scanning imaging technology apparatus cannot be used and combined with associated apparatus/devices in existing airport, railway station, customs and other key facilities and spots.

Furthermore, a single-scanning active millimeter wave three dimensional holographic scan imaging apparatus may detect only one side of a human body at one time and thus needs twice scanning so as to achieve a complete inspection on the passenger to be inspected. During twice scanning, the passenger to be inspected has to turn around. The safety inspection process is thus complicated and the speed of the inspection is low.

In order to achieve human body security inspection, it is desirable to provide a millimeter wave holographic scan imaging apparatus, which at least alleviate or eliminate at least one aspect of the above technical problems.

SUMMARY OF THE INVENTION

It is an object of the present invention to solve at least one aspect of the above technical problems and defects in the prior art.

Accordingly, an object of the present invention is to provide a millimeter wave holographic scan imaging apparatus, which has a simplified structure and achieves stable imaging quality.

Another of the objects of the present invention is to provide a millimeter wave holographic scan imaging apparatus, which performs scanning with increased efficiency and is optimized in occupying floor area.

According to an aspect of the present invention, there is provided a millimeter wave holographic scan imaging apparatus for inspecting a human body, comprising: a first millimeter wave transceiver device comprising a first millimeter wave transceiver antenna array for transmitting and receiving a first millimeter wave signal; a second millimeter wave transceiver device, which comprises a second millimeter wave transceiver antenna array for transmitting and receiving a second millimeter wave signal, and is configured in opposite direction with relation to the first millimeter wave transceiver device; a connection member connecting the first millimeter wave transceiver device to the second millimeter wave transceiver device; and a drive device for driving one of the first and the second millimeter wave transceiver devices such that the first millimeter wave transceiver device and the second millimeter wave transceiver device move in opposite directions.

Further, the millimeter wave holographic scan imaging apparatus further comprises: a first guide track, to which the first millimeter wave transceiver device is slidably connected so as to perform a first scanning to an object to be inspected therealong; and a second guide track, to which the second millimeter wave transceiver device is slidably connected so as to perform a second scanning for an object to be inspected therealong.

In a specific embodiment, the connection member comprises: a first flexible connection member respectively connected to the first millimeter wave transceiver device and the second millimeter wave transceiver device at a first side; a second flexible connection member respectively connected to the first millimeter wave transceiver device and the second millimeter wave transceiver device at a second side opposite to the first side, thereby constituting a quadrilateral structure.

Specifically, the millimeter wave holographic scan imaging apparatus further comprises: an arch leg assembly, which is constructed by a horizontal truss and a first and a second vertical support pillar to form a substantial arch shape structure; wherein, the first guide track and the second guide track are vertically fixed inside of the first and the second vertical support pillars, respectively.

Furthermore, the millimeter wave holographic scan imaging apparatus further comprising: a first slide block support plate assembly, by which the first millimeter wave transceiver device is connected slidably to the first guide track respectively, so as to move along the first guide track to perform the first scanning to the object to be inspected; and, a second slide block support plate assembly, by which the second millimeter wave transceiver device is connected slidably to the second guide track respectively, so as to move along the second guide track to perform the second scanning to the object to be inspected.

In the above technical solution, the first and the second slide block support plate assemblies may respectively include: a rear wing plate, the first flexible connection member being respectively connected to the rear wing plate of the first and the second slide block support plate assemblies so as to respectively connect to the first millimeter wave transceiver device and the second millimeter wave transceiver device at the first side; a front wing plate, the second flexible connection member being respectively connected to the front wing plate of the first and the second slide block support plate assemblies so as to respectively connect to the first millimeter wave transceiver device and the second millimeter wave transceiver device at the second side opposite to the first side; and a saddle, to which the rear wing plate and the front wing plate are fixed.

Specifically, the first millimeter wave transceiver device and the second millimeter wave transceiver device are respectively mounted on the saddle of the first and the second slide block support plate assemblies.

Preferably, the millimeter wave holographic scan imaging apparatus is characterized by further comprising: first fixed pulley blocks fixed at either side of the arch leg assembly device, respectively, wherein the first flexible connection member is connected to the rear wing plate of the first and second slide block support plate assembly via the first fixed pulley blocks; second fixed pulley blocks fixed at either side of the arch leg assembly device, respectively, wherein the second flexible connection member is connected to the front wing plate of the first and second slide block support plate assembly via the second fixed pulley block.

In the above technical solution, the driving device comprises: a reduction electrical motor; a synchronous pulley coupled and connected to an output shaft of the reduction electrical motor; and a synchronous cog belt engaged to gear tooth of the synchronous pulley so as to rotate under action of the reduction electrical motor.

Specifically, the millimeter wave holographic scan imaging apparatus further comprises: a pressing block for fixedly connecting the synchronous pulley to the saddle of one of the slide block support plate assemblies; wherein, the driving device is configured to drive the one of the slide block support plate assemblies, thereby the other of the slide block support plate assemblies being driven via the first and second flexible connection members connected between two slide block support plate assemblies, to move up-down in an opposite direction.

Alternatively, a plane, in which the first and the second millimeter wave transceiver devices are located, is configurable to be parallel to or subtend an angle with relation to a horizontal plane.

Alternatively, the first and the second millimeter wave antenna arrays may be arranged in manner of strange line, serration line or curve line, so as to form the first and the second millimeter wave transceiver devices.

Furthermore, the millimeter wave holographic scan imaging apparatus further comprises: a data processing device configured to be wirelessly or wire coupled to the first and the second millimeter wave transceiver devices to receive scanning data therefrom and generate a millimeter wave holographic scan image; and, a display device configured to communicate with the data processing device, for receiving and displaying the millimeter wave holographic scan image from the data processing device.

Furthermore, the millimeter wave holographic scan imaging apparatus further comprises: a control device configured to generate a control signal and transmit it to the driving device such that the driving device drives the first millimeter wave transceiver device and the second millimeter wave transceiver device to move.

Preferably, during the whole process of the first millimeter wave transceiver device and the second millimeter wave transceiver device together performing a scanning to an object to be inspected, the first millimeter wave signal and the second millimeter wave signal are configured to be transmitted in different frequency.

Preferably, during the whole process of the first millimeter wave transceiver device and the second millimeter wave transceiver device together performing a scanning to an object to be inspected, the first millimeter wave transceiver antenna array and the second millimeter wave transceiver antenna array are configured to be transmitted in different timing.

In an embodiment, the pressing block is configured to have an inward concave mating portion complementary in shape to an outward protruding tooth portion of the synchronous cog belt, the outward protruding tooth portion of the synchronous cog belt being depressed in the inward concave mating portion of the pressing block. The saddle of the slide block support plate assembly is provided with an aperture. After the outward protruding tooth portion of the synchronous cog belt having been depressed in the inward concave mating portion of the pressing block, they are fixedly connected to the saddle of the slide block support plate assembly by a fastener.

Furthermore, the millimeter wave holographic scan imaging apparatus further comprises: an impact block mounted on the slide block support plate assembly, which moves up-down together with the slide block support plate assembly; and a limit switch and a proximity switch disposed at either end position of the second guide track, the impact block and the proximity switch cooperate with each other so as to determine a zero position and a terminal position of the slide block support plate assemblies, and the impact block and the limit switch cooperate with each other so as to determine a limit position of the slide block support plate assembly.

More specifically, the millimeter wave holographic scan imaging apparatus further comprises: a housing, which is configured to, together with the arch leg assembly, enclose a scanning space for performing scanning and imaging for an object to be inspected.

In an embodiment, the data processing device is located in a top space above the scanning space.

By the above technical solution according to the present invention, at least one aspect of the present invention has advantages as below:

With relation to the traditional inspection, the millimeter wave inspection imaging technology may achieve penetration through human clothing, emit radiation in small dose while enable identification of various metal and nonmetal contraband articles.

At least one aspects of the present invention may be achieved by at least two millimeter wave transceiver devices to perform a two-side scanning to an object to be inspected, i.e., achieve a front and back sides scanning to human body at one time, so as to reduce inspection time. With the above construction, the scanning speed and imaging accuracy of the millimeter wave inspection apparatus can be improved while simplifying scanning operation and improving flexibility of the application of the apparatus.

The technical scheme according to the present invention is designed to perform a planar scanning while having a compact structure, occupying rather small floor area. Particularly, the millimeter wave holographic scan imaging apparatus can be adopted to be combined with associated apparatus/devices in existing airport, railway station, customs and other important departments without modifying and altering the existing apparatus.

BRIEF DESCRIPTION OF THE DRAWINGS

These and other aspects as well as advantages of the present invention will become apparent and readily understood from the description of the preferred embodiments taking in conjunction with the accompanying drawings, in which.

DETAILED DESCRIPTION OF THE PREFERRED EMBODIMENTS

Figure 1:
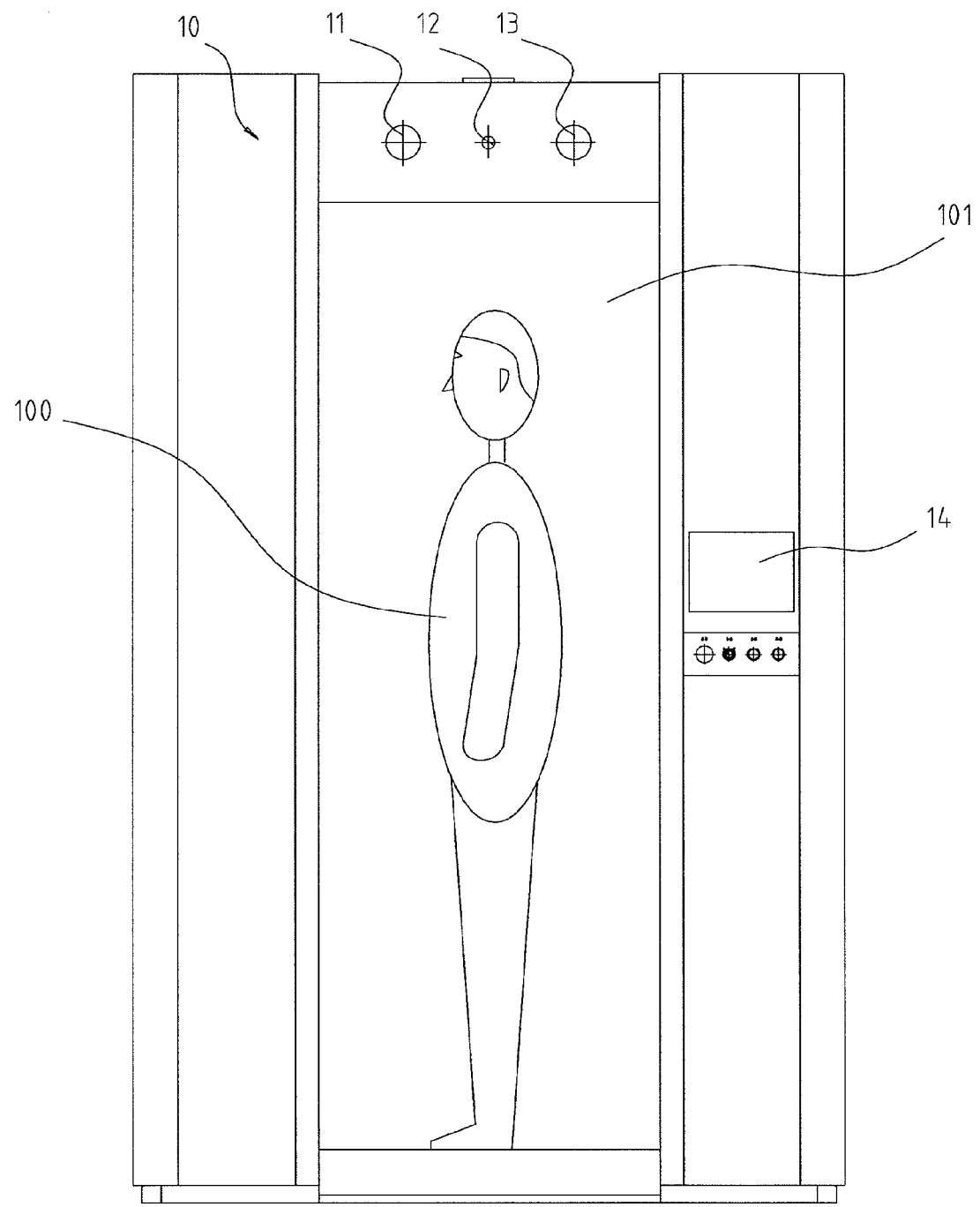
FIG. 1 shows schematically a figuration of a millimeter wave holographic scan imaging apparatus 1 for human body inspection according to an embodiment of the present invention.

Technical solutions of the present invention will be described hereinafter in more detail by the way of embodiment with reference to figures of the attached drawings, wherein the same or like reference numerals refer to the same or like elements throughout the specification. The explanation of the embodiment of the present invention with referring to the accompanying drawings is intended to expound the general inventive concept of the present invention, rather than being construed as limiting to the present invention.

Figure 2:
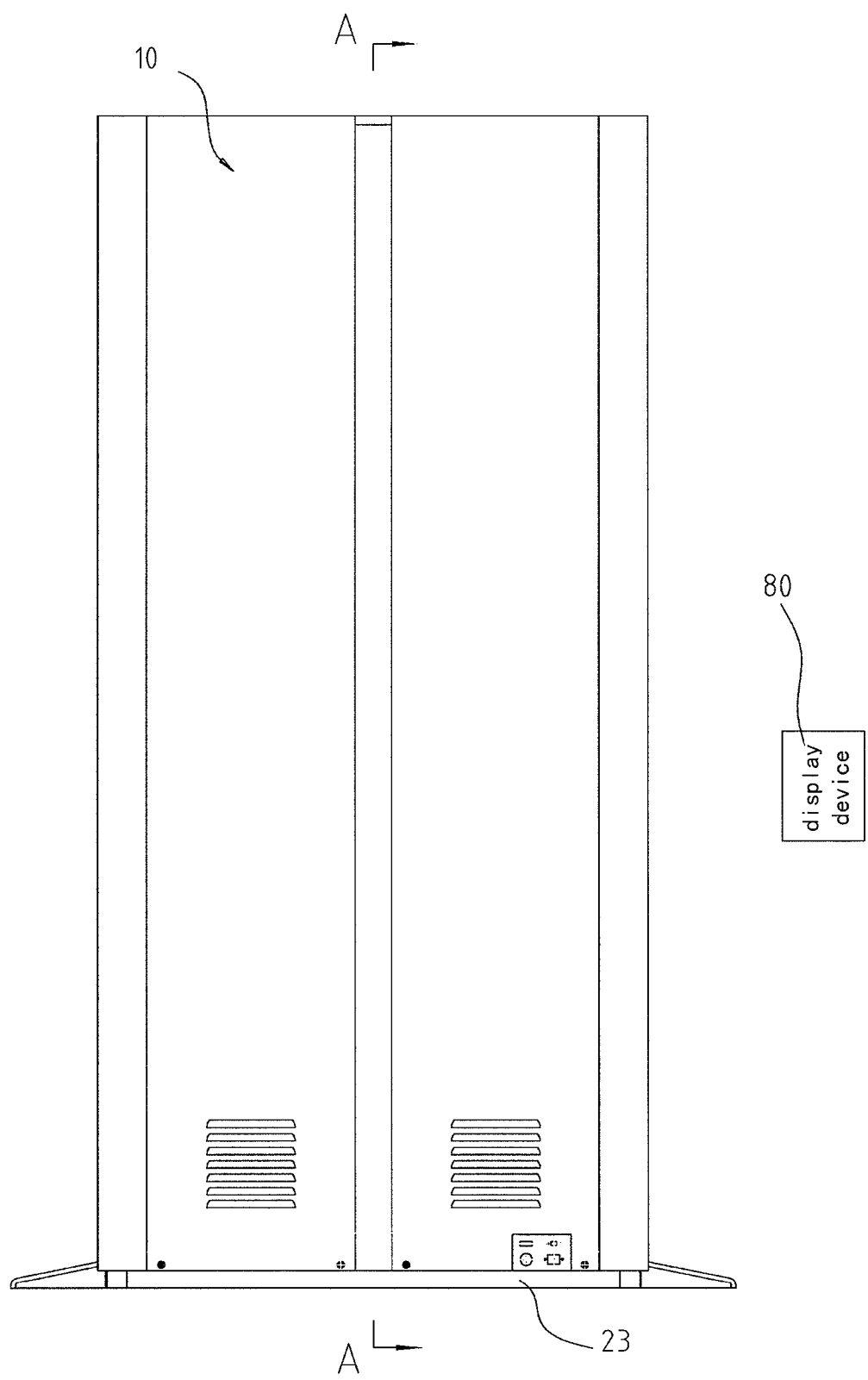
FIG. 2 shows a left view of the figuration of the millimeter wave holographic scan imaging apparatus 1 for human body inspection in FIG. 1.
Figure 3:
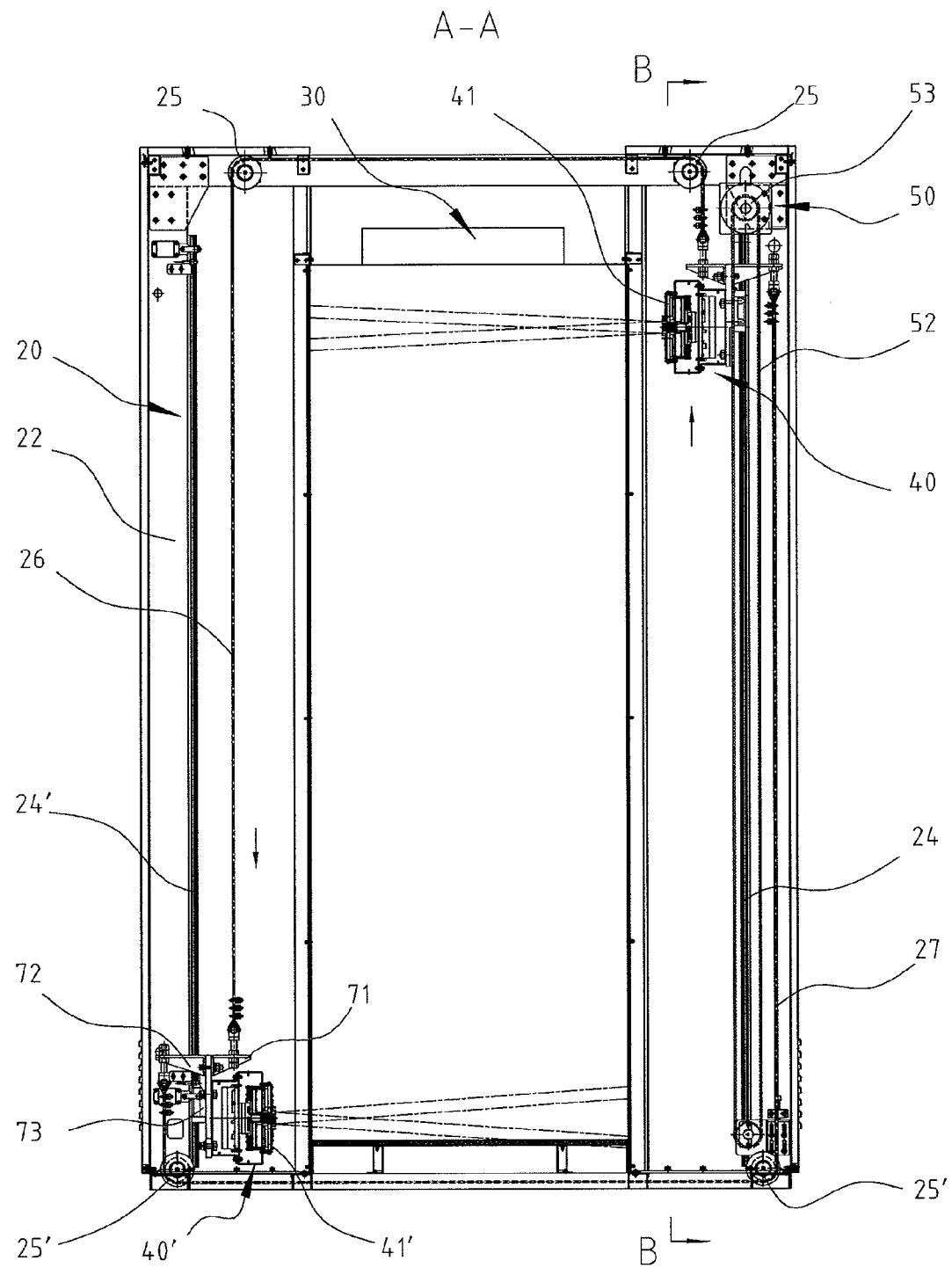
FIG. 3 shows a cut-away view taken along A-A line in FIG. 2.

FIG. 1 shows schematically a figuration of a millimeter wave holographic scan imaging apparatus 1 for human body inspection according to an embodiment of the present invention. As shown in FIGS. 1-4, the millimeter wave holographic scan imaging apparatus 1 for human body inspection according to a preferred embodiment of the present invention may include a housing 10, an arch leg assembly 20, a data processing device 30, a millimeter wave transceiver device 40, a driving device 50, a control device 60, etc. As shown in FIGS. 1-3, the housing 10 and the arch leg assembly 20 together enclose a scanning space 101 for performing a scanning and imaging for an object 100 to be inspected.

As illustrated in FIGS. 1-3, the millimeter wave holographic scan imaging apparatus 1 for human body inspection according to the present invention includes a first millimeter wave transceiver device 40, which comprises a first millimeter wave transceiver antenna array 41 for transmitting and receiving a first millimeter wave signal; a second millimeter wave transceiver device 40', which comprises a second millimeter wave transceiver antenna array 41' for transmitting and receiving a second millimeter wave signal and is configured in opposite direction with relation to the first millimeter wave transceiver device; a connection member, such as a steel cable 26, 27, which connects the first millimeter wave transceiver device 40 and the second millimeter wave transceiver device 40'; and a drive device 50, which drives one of the first and the second millimeter wave transceiver devices such that the first millimeter wave transceiver device (40) and the second millimeter wave transceiver device (40') move in opposite directions.

Figure 9B:
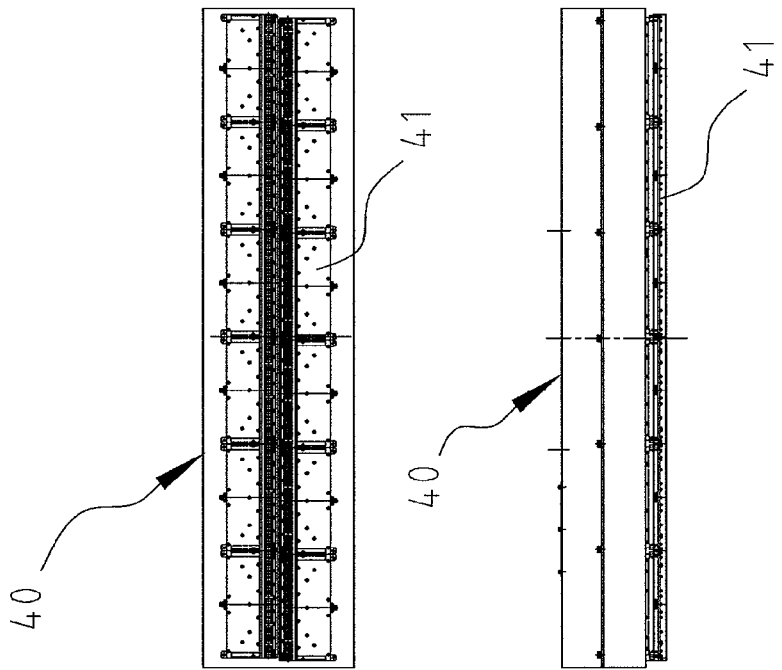
FIG. 9 is a schematic view of the millimeter wave transceiver device 40 according to an embodiment of the present invention, wherein a millimeter wave transceiver antenna array 41 of the millimeter wave transceiver device 40 is shown in FIG. 9A to be arranged in a straight line and a millimeter wave transceiver antenna array 41 of the millimeter wave transceiver device 40 is shown in FIG. 9B to be arranged in a serration line.
Figure 9A:
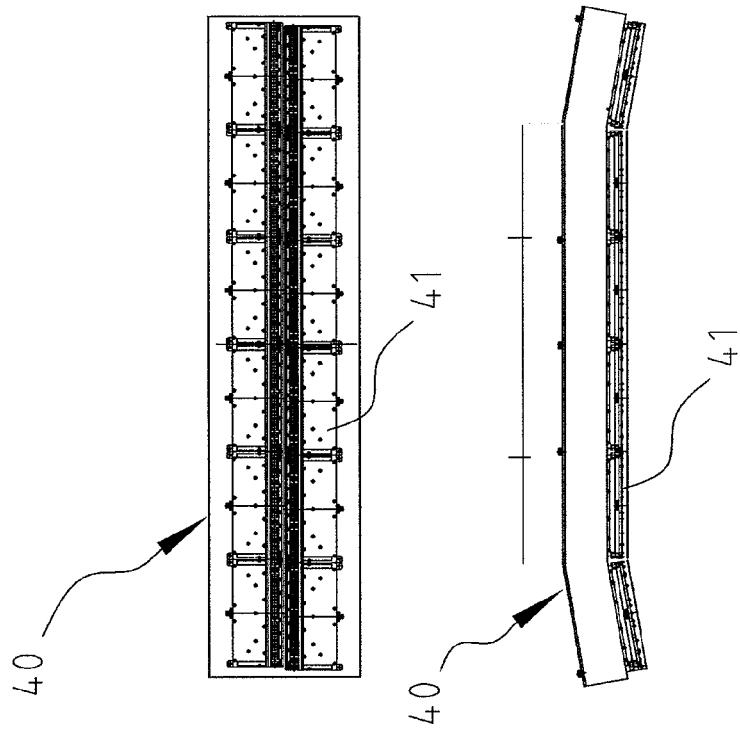

In the above embodiment, as shown in FIG. 9A, a plurality of millimeter wave transceiver antenna arrays 41 are arranged in a straight line so as to form a millimeter wave transceiver device 40. However, the present invention is not limited to this case. For example, a plurality of millimeter wave transceiver antenna arrays 41 may also be arranged around the inspected object 100 in manner of serration line, as shown in FIG. 9B, to form a first and a second millimeter wave transceiver device 40, 40', respectively. In another embodiment, a plurality of millimeter wave transceiver antenna arrays 41 may also be arranged in circular arc or other curved line around the object 100 as a center. Due to arrangement in manner of serration line or circular arc, holographic scan imaging performance of the millimeter wave holographic scan apparatus may be further improved.

In an embodiment, the connection member includes an upper hanging steel cable 26, as a first flexible connection member, which is connected to the first millimeter wave transceiver device 40 and the second millimeter wave transceiver device 40', respectively, at a first side, such as, the upper side as shown in FIG. 3; and a lower pulling steel cable 27, as a second flexible connection member, which is connected to the first millimeter wave transceiver device 40 and the second millimeter wave transceiver device 40', respectively at a second side opposite to the first side, i.e., the lower side as shown in FIG. 3.

Furthermore, in a preferred embodiment, during the whole process of the first millimeter wave transceiver device 40 and the second millimeter wave transceiver device 40' together performing a scanning to an object to be inspected, the first millimeter wave signal and the second millimeter wave signal are configured to be transmitted in different frequency. During the whole process of the first millimeter wave transceiver device 40 and the second millimeter wave transceiver device 40' together performing a scanning to an object to be inspected, the first millimeter wave transceiver antenna array 41 and the second millimeter wave transceiver antenna array 41' are configured to be transmitted in different timing. By this way, it is possible to weaken or avoid signal interference between the first millimeter wave transceiver device 40 and the second millimeter wave transceiver device 40'.

As illustrated in FIGS. 2-3, in the housing 10 of the millimeter wave holographic scan imaging apparatus 1, an arch leg assembly 20 is provided, which includes a horizontal truss 21 and a first and a second vertical support pillar 22, 22 so as to form an arch shape structure. As shown in FIG. 2, in an embodiment, the horizontal truss 21 and the first and the second vertical support pillars 22, 22 are together fixed on the base mount 23.

The first guide track 24 and the second guide track 24', such as, a linear slide rail 24, are respectively vertically fixed inside of the first and the second vertical support pillars 22, 22. The first millimeter wave transceiver device 40 is connected slidably to the first guide track 24, such as, by a first slide block support plate assembly 70, so as to move along the first guide track 24 to perform a first scanning to the object 100 to be inspected, such as, a human body. The second millimeter wave transceiver device 40' is connected slidably to the second guide track 24', such as, by a second slide block support plate assembly 70', so as to move along the second guide track 24' to perform a second scanning to the human body to be inspected.

Further, first fixed pulley blocks 25 are respectively fixed at either side of the arch leg assembly 20, wherein the upper hanging steel cable 26 is connected to the rear wing plate 71 of the first and second slide block support plate assemblies 70, 70' via the first fixed pulley blocks 25. Second fixed pulley blocks 25 are fixed at either side of the arch leg assembly device 20, respectively, wherein the second flexible connection member 27 is respectively connected to the front wing plate 72 of the first and second slide block support plate assembly 70, 70' via and around the second fixed pulley blocks 25.

In the above technical solution, the two slide block support plate assemblies 70 are installed on the two linear guide track 24 through two slide blocks 74, so as to move up-down in vertical direction as shown in FIG. 3. The redirection fixed pulleys 25, such as, four fixed pulleys as shown in FIG. 3, are mounted either side of the arch leg assembly 22, so as to form a quadrangle pulley block. The driving device 50 is configured to drive the one of the slide block support plate assemblies 70, thereby the other of the slide block support plate assemblies 70 being driven via the upper hanging steel cable 26 connected between two slide block support plate assemblies 70 to move up-down in an opposite direction. The two slide block support plate assemblies 70 together with the upper hanging steel cable 26 and the lower pulling steel cable 27 form a endless-loop rigid structure through redirection fixed pulley block 25, thereby avoiding vibration caused during stopping and thus improving imaging performance of the millimeter wave holographic scan imaging apparatus 1 for human body inspection.

Figure 7:
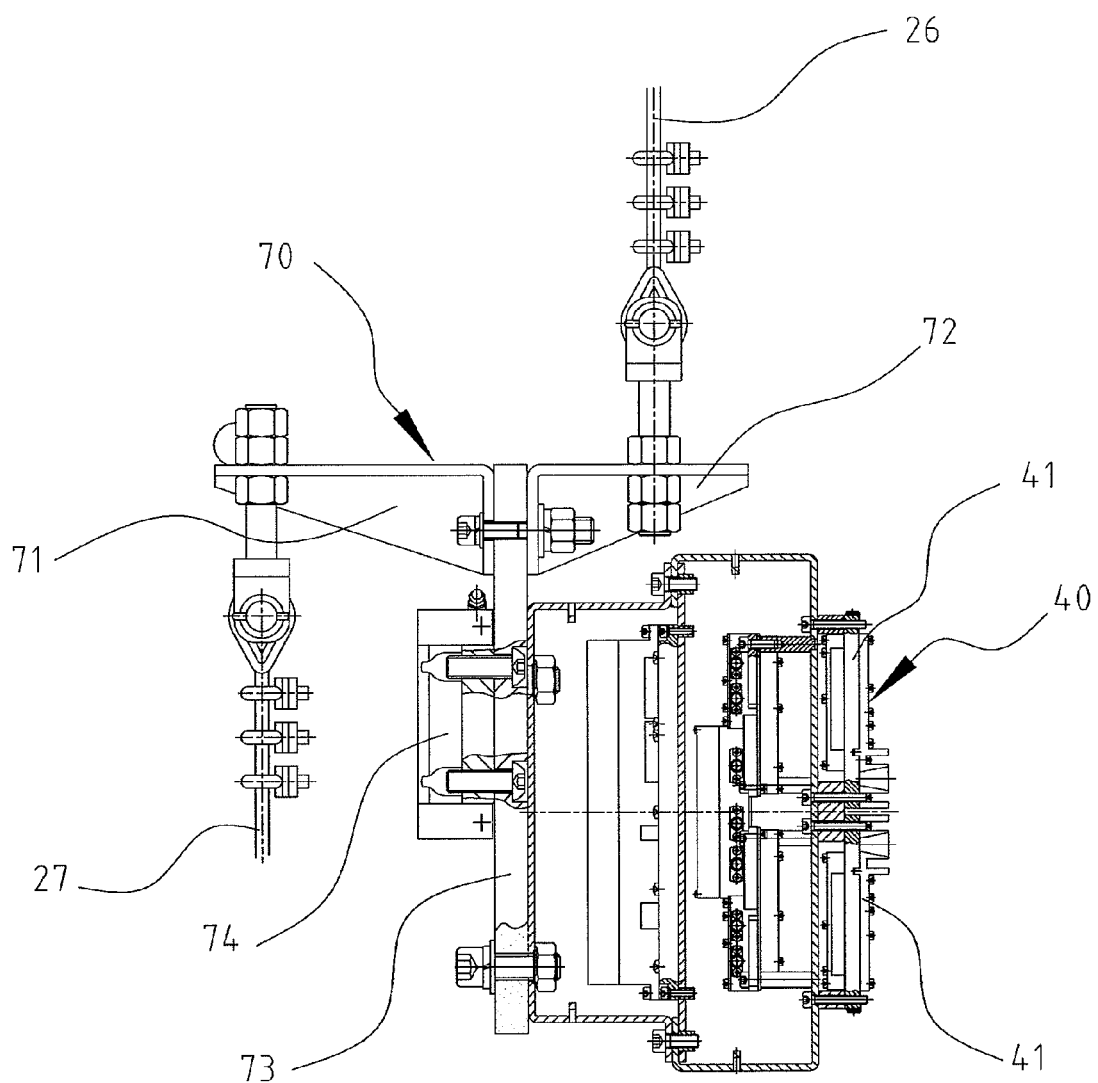
FIG. 7 shows schematically a structural view of a slide block support plate assembly 70 in the millimeter wave holographic scan imaging apparatus 1.

FIG. 7 shows schematically a structural view of a slide block support plate assembly 70 in the millimeter wave holographic scan imaging apparatus 1. As shown in FIG. 7, the first and the second slide block support plate assemblies 70, 70' respectively include: a rear wing plate 71, in which the first flexible connection member 26 are respectively connected to the rear wing plate 71 of the first and the second slide block support plate assemblies 70, 70' so as to respectively connect to the first millimeter wave transceiver device and the second millimeter wave transceiver device at a first side; a front wing plate 72, in which the second flexible connection member 27 are respectively connected to the front wing plate 72 of the first and the second slide block support plate assemblies 70, 70' so as to respectively connect to the first millimeter wave transceiver device and the second millimeter wave transceiver device at a second side opposite to the first side; and, a saddle 73, to which the rear wing plate 71 and the front wing plate 72 are fixed. The first millimeter wave transceiver device 40 and the second millimeter wave transceiver device 40' are mounted respectively on the saddle 73 of the first and the second slide block support plate assemblies 70, 70'. In the embodiment, two same millimeter wave transceiver device 40, 40' are respectively mounted on the same two slide block support plate assemblies 70, 70' while the two millimeter wave transceiver devices 40, 40' are balanced to each other by their gravities, thereby effectively reducing required drive power.

Figure 8:
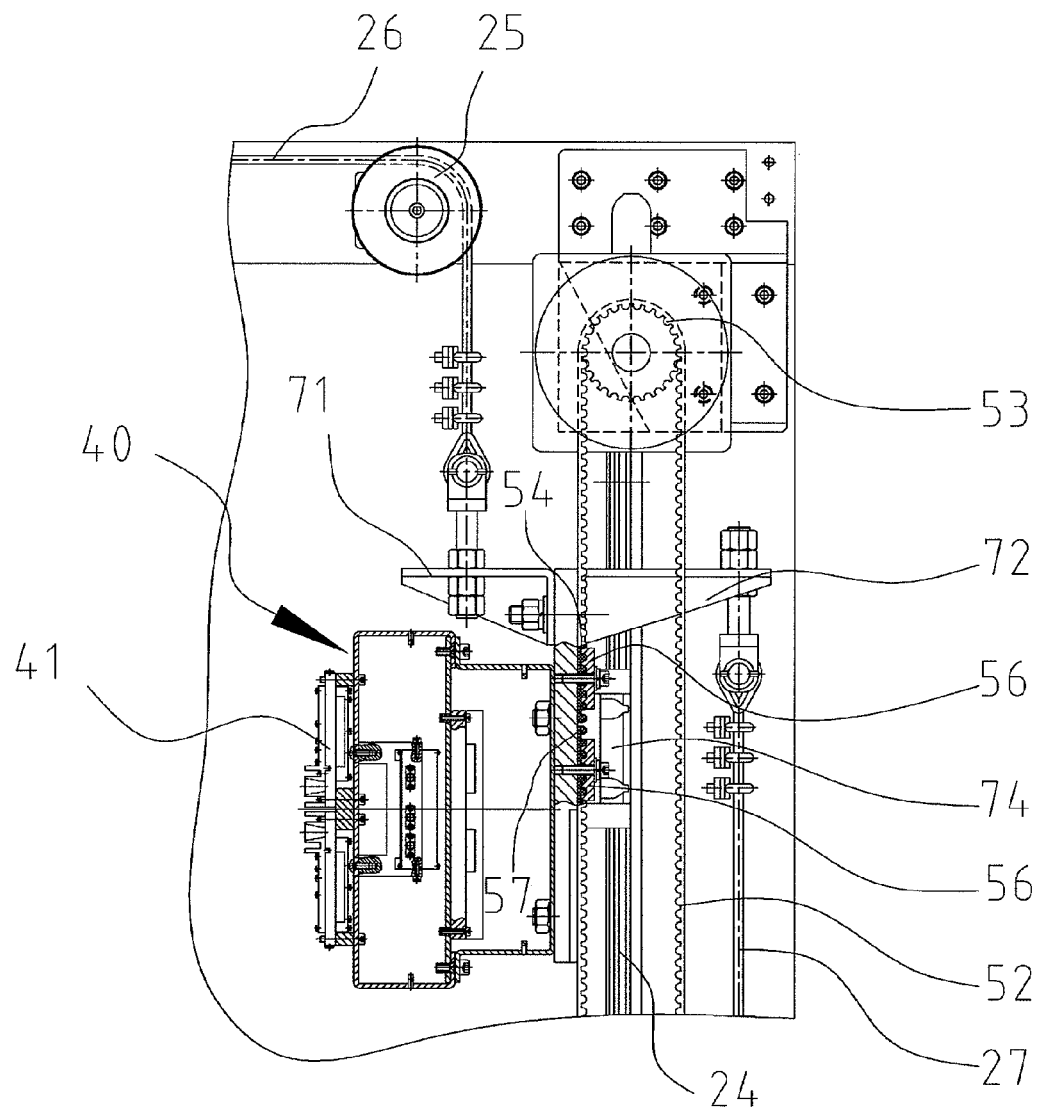
FIG. 8 shows schematically a driving device 50 and a connection manner between the driving device 50 and the slide block support plate assembly 70 in the millimeter wave holographic scan imaging apparatus 1.

FIG. 8 shows schematically a driving device 50 and a connection manner between the driving device 50 and the slide block support plate assembly 70 in the millimeter wave holographic scan imaging apparatus. With reference to FIGS. 3-8, the driving device 50 includes a reduction electrical motor 51, a synchronous pulley 53 coupled to an output shaft of the reduction electrical motor 51; and a synchronous cog belt 52 engaged with gear tooth of the synchronous pulley 53 so as to rotate under action of the reduction electrical motor 51. In order to achieve driving action transmission from the reduction electrical motor 51 to the slide block support plate assembly 70 so as to the other slide block support plate assembly 70', a transmission member, such as a pressing block 56, is provided to fixedly couple the synchronous pulley 53 to the saddle 73 of one of the slide block support plate assembly 70. The drive device 50 drives one of the slide block support plate assemblies 70, thereby the other of the slide block support plate assemblies 70 being driven via the first and second flexible connection members connected between two slide block support plate assemblies 70, to move up-down in an opposite direction.

In the shown embodiments, the first and the second millimeter wave transceiver devices 40' are configured to be parallel to a horizontal plane so as to scan in a vertical direction. However, the present invention is not limited to this case. For example, the first and the second millimeter wave transceiver devices 40' may also be configured to subtend a certain angle with respect to the horizontal plane.

Specifically, as shown in FIG. 8, the pressing block 56 is configured to have an inward concave mating portion 57 complementary in shape to an outward protruding tooth portion 54 of the synchronous cog belt 52. During assembling, the outward protruding tooth portion 54 of the synchronous cog belt 52 is depressed in the inward concave mating portion 57 of the pressing block 56. Meanwhile, the saddle 73 of the slide block support plate assembly 70 is provided with an aperture, such as, a threaded hole. After the outward protruding tooth portion 54 of the synchronous cog belt 52 having been depressed in the inward concave mating portion 57 of the pressing block 56, they are further securely connected to the saddle 73 of the slide block support plate assembly 70 by a fastener, such as, a screw.

As shown in FIG. 3, the millimeter wave holographic scan imaging apparatus for inspecting a human body according to the present invention further includes a data processing device 30 located on top of the scanning space 101. The data processing device 30 is configured to be wirelessly or wire coupled to the first and the second millimeter wave transceiver devices 40, 40' to receive scanning data from the first and the second millimeter wave transceiver devices and generate a millimeter wave holographic scan image. In FIG. 3, the data processing device 30 is located on top of the scanning space 101. However, it is appreciated that the present invention is not limited to this case. In particular, when data communication is performed in wireless manner, the data processing device 30 may be located at any suitable position.

As shown in FIG. 1, the apparatus further includes a display apparatus 80, which communicates with the data processing device 30 for receiving and displaying millimeter wave holographic scan image from the data processing device 30. In case the display device 80 communicates data with the data processing device 30 in wireless manner, the display device 80 may be located at any suitable position.

Figure 4:
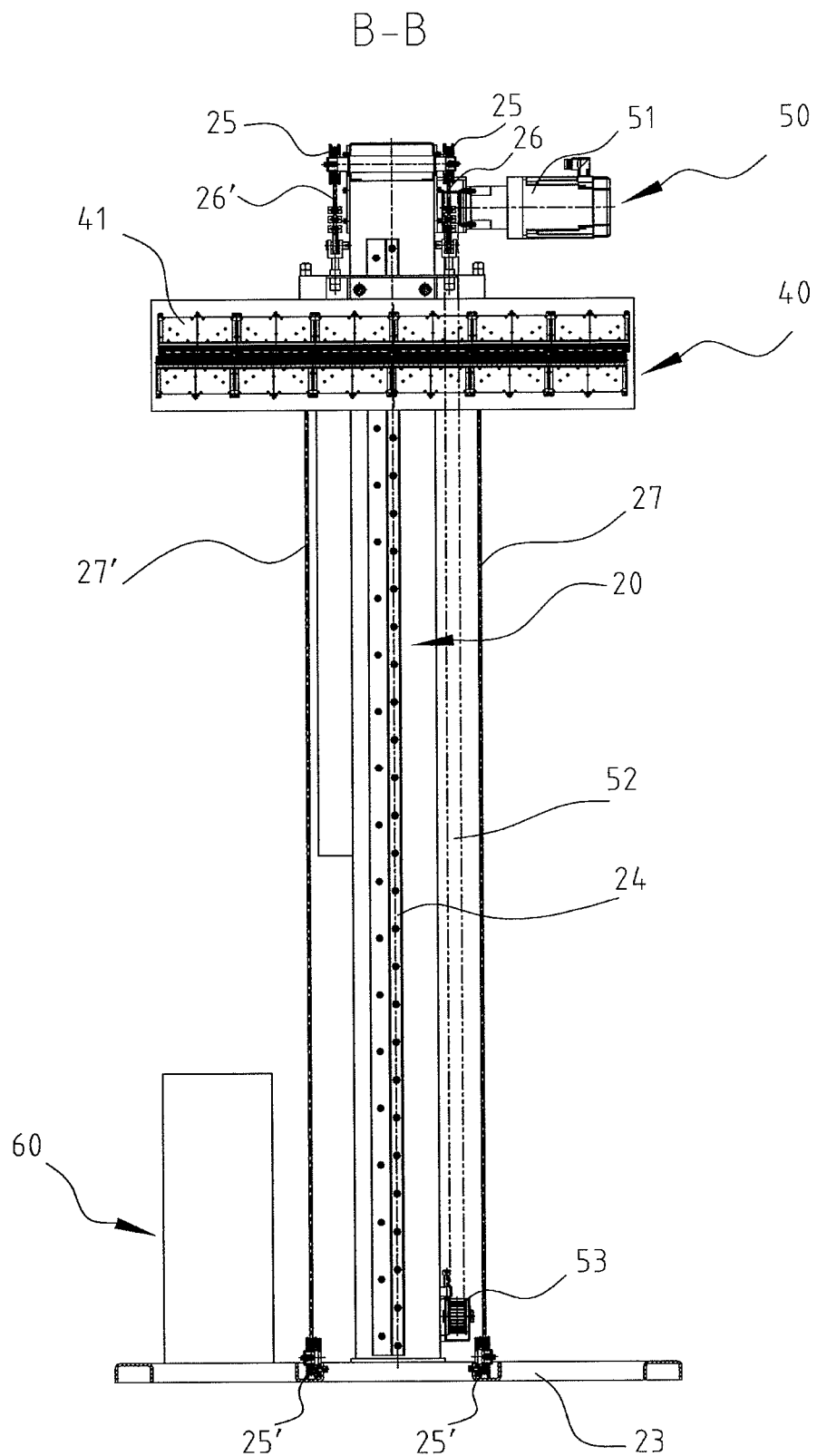
FIG. 4 shows a cut-away view taken along B-B line in FIG. 3.

As shown in FIG. 4, the millimeter wave holographic scan imaging apparatus further includes a control device 60 for generating a control signal and transmitting it to the driving device 50 such that the driving device drives the first millimeter wave transceiver device 40 and the second millimeter wave transceiver device 40' to move.

Figure 5:
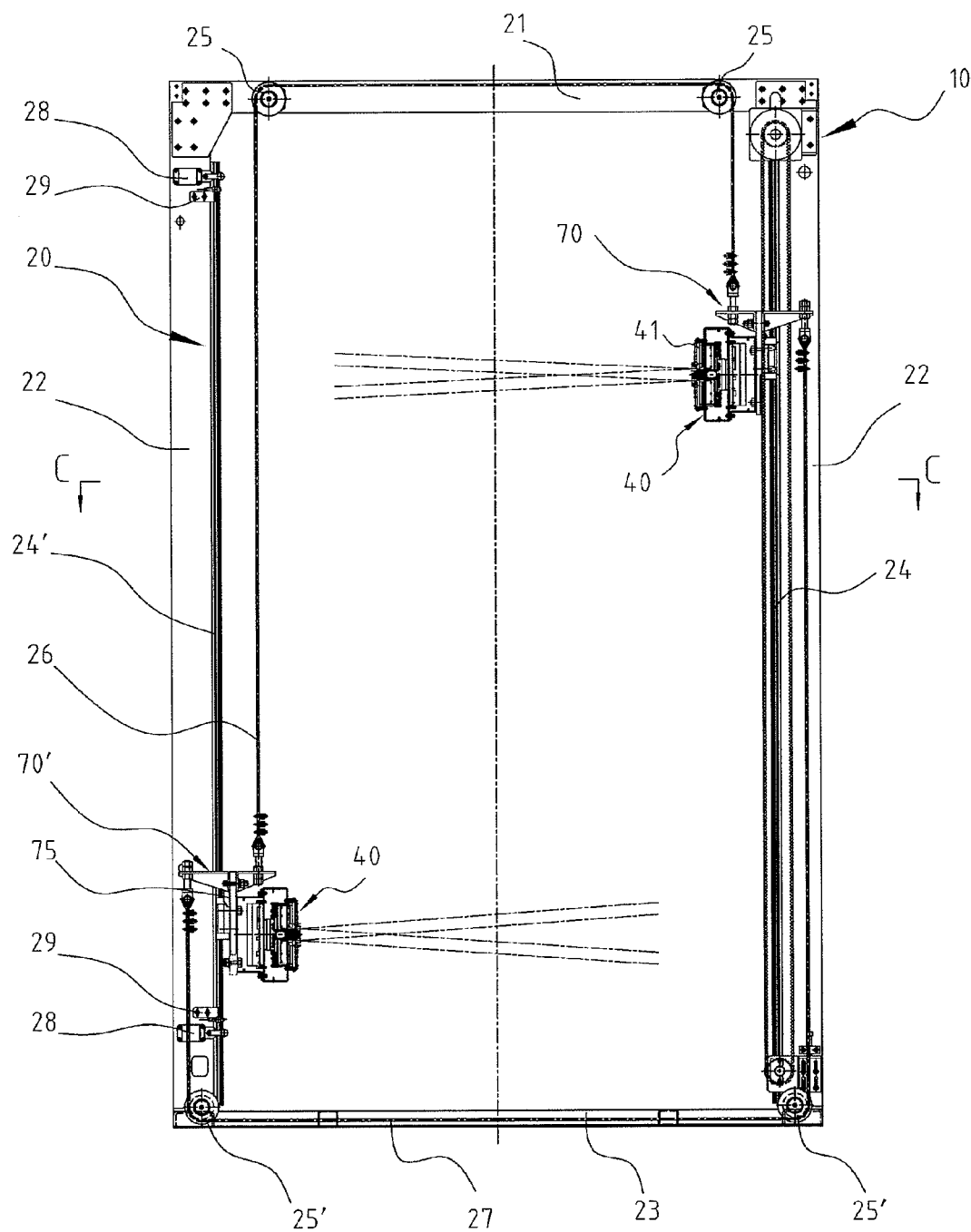
FIG. 5 shows schematically a structural view of an arch leg assembly 20 in the millimeter wave holographic scan imaging apparatus 1 in FIG. 5.
Figure 6:
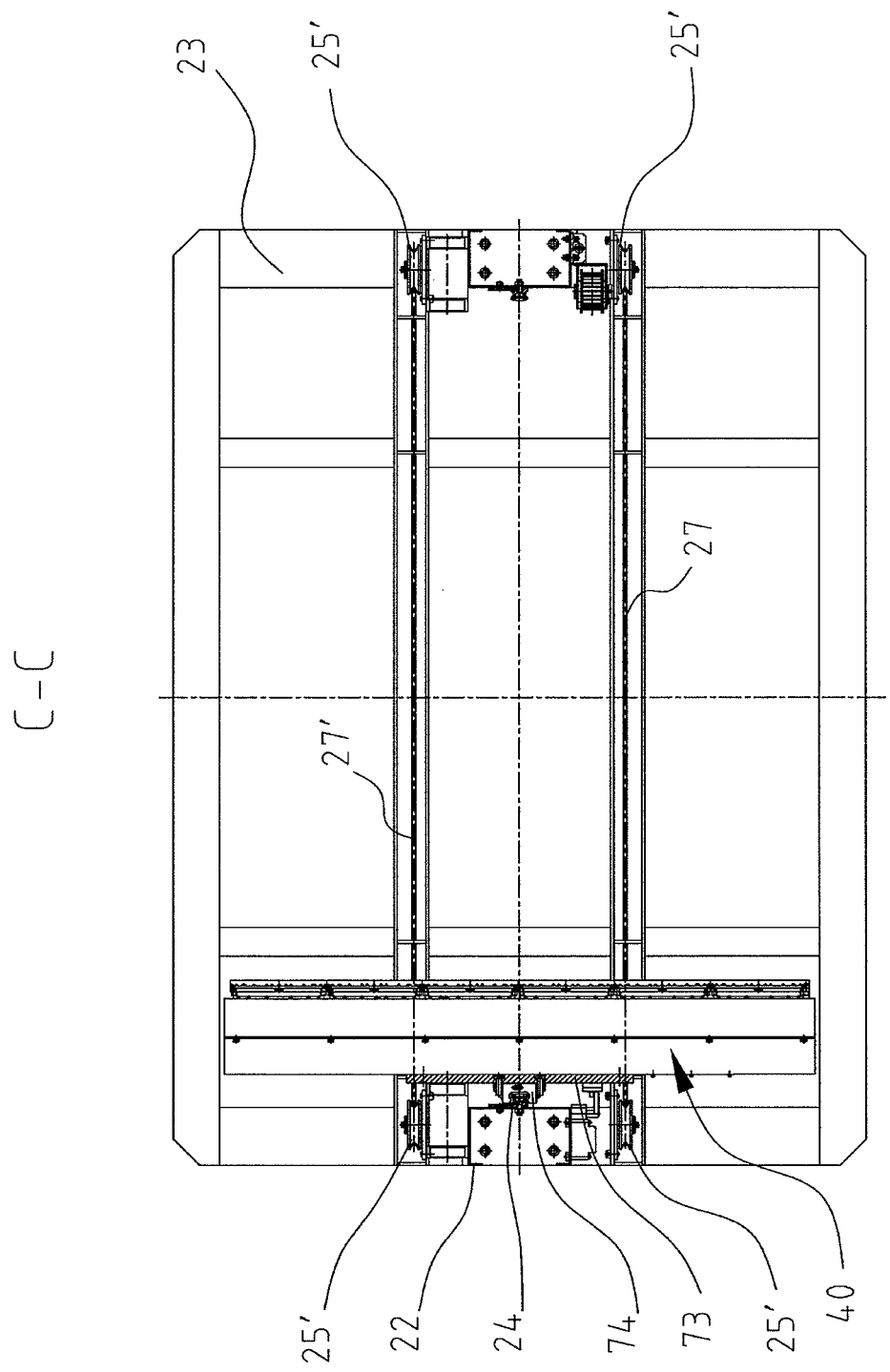
FIG. 6 is a cut-away view taken along C-C line in FIG. 5.

As shown in FIG. 5, the millimeter wave holographic scan imaging apparatus further includes an impact block 75, which is mounted on and thus moves up-down together with the slide block support plate assembly 70 or 70'. The impact block 75 cooperates with, such as, the proximity switch 29 located on two ends of the guide track 24' so as to determine a zero position and a terminal position of the slide block support plate assembly 70 or 70'. Meanwhile, the impact block 75 and, such as, the limit switch 28, located on two ends of the guide track 24, cooperate with each other to determine a limit position of the slide block support plate assembly 70 or 70', thereby preventing the slide block support plate assembly 70 or 70' from moving beyond its limit position and preventing damage from the apparatus.

In addition, as shown in FIG. 1, the millimeter wave holographic scan imaging apparatus according to the present invention further includes a scan-indicating light 11, a buzzer 12 and a work-indicating light 13, which are located above the scanning space 101. At a side of the scanning space 101, a LCD touch screen 14 is provided for indicating and manual inputting by security personnel to control operation of the apparatus. In use, a human 100 to be inspected enters the scanning space 101 and stands therein. Then, the scan-indicating light 11 lights while the two millimeter wave transceiver devices 40 in the apparatus start to scan in the vertical direction where one of the millimeter wave transceiver devices 40 moves upward and the other one moves downward. After scanning, a holographic scan millimeter wave image is generated for the object. Preferably, after a millimeter wave holographic scan image for human body or item having been generated, it is possible to automatically identify whether the human body carry suspicious articles or any suspicious items are hidden in the object to be inspected—and the position of the suspicious articles. The identification result can be outputted, for example, by way of sound information. For example, a buzzer 12 gives out sound information and the inspected passenger 100 may then leave or go through a further risk inspection. With the above configuration, it is possible to rapidly detect suspicious articles and monitor security risks customs. This is particularly helpful where it is required to fast determine or monitor risk in places such as airport, customs etc.

Although several embodiments of the general inventive concept are illustrated and explained, it would be appreciated by those skilled in the art that modifications and variations may be made in these embodiments without departing from the principles and spirit of the general inventive concept of the disclosure, the scope of which is defined in the appended claims and their equivalents.

What is claimed is:

1. A millimeter wave holographic scan imaging apparatus for inspecting a human body, comprising:
a first millimeter wave transceiver device comprising a first millimeter wave transceiver antenna array for transmitting and receiving a first millimeter wave signal;
a second millimeter wave transceiver device, including a second millimeter wave transceiver antenna array for transmitting and receiving a second millimeter wave signal, and is configured in opposite direction with relation to the first millimeter wave transceiver device;
a connection member for connecting the first millimeter wave transceiver device to the second millimeter wave transceiver device; the connection member comprising:
a first flexible connection member respectively connected to the first millimeter wave transceiver device and the second millimeter wave transceiver device at a first side;
a second flexible connection member respectively connected to the first millimeter wave transceiver device and the second millimeter wave transceiver device at a second side opposite to the first side, thereby constituting a quadrilateral structure;
a first guide track, to which the first millimeter wave transceiver device is slidably connected so as to perform a first scanning to an object to be inspected therealong;
a second guide track, to which the second millimeter wave transceiver device is slidably connected so as to perform a second scanning for an object to be inspected therealong;
a drive device, which drives one of the first and the second millimeter wave transceiver devices such that the first millimeter wave transceiver device and the second millimeter wave transceiver device move in opposite directions;
an arch leg assembly, constructed by a horizontal truss and a first and a second vertical support pillar to form a substantial arch shape structure;
the first guide track and the second guide track being vertically fixed inside of the first and the second vertical support pillars, respectively;
a first slide block support plate assembly, by which the first millimeter wave transceiver device is connected slidably to the first guide track respectively, so as to move along the first guide track to perform the first scanning to the object to be inspected; and
a second slide block support plate assembly, by which the second millimeter wave transceiver device is connected slidably to the second guide track respectively, so as to move along the second guide track to perform the second scanning to the object to be inspected;
wherein the first and the second slide block support plate assemblies respectively include:
a rear wing plate, wherein, the first flexible connection member is respectively connected to the rear wing plate of the first and the second slide block support plate assemblies so as to respectively connect to the first millimeter wave transceiver device and the second millimeter wave transceiver device at a first side;
a front wing plate, wherein the second flexible connection member is respectively connected to the front wing plate of the first and the second slide block support plate assemblies so as to respectively connect to the first millimeter wave transceiver device and the second millimeter wave transceiver device at a second side opposite to the first side; and,
a saddle, to which the rear wing plate and the front wing plate are fixed.

2. The millimeter wave holographic scan imaging apparatus for inspecting a human body according to claim 1, wherein,
the first millimeter wave transceiver device and the second millimeter wave transceiver device are respectively mounted on the saddle of the first and the second slide block support plate assemblies.

3. The millimeter wave holographic scan imaging apparatus for inspecting a human body according to claim 1, further comprising:
first fixed pulley blocks fixed at either side of the arch leg assembly device, respectively, wherein the first flexible connection member is connected to the rear wing plate of the first and second slide block support plate assembly via the first fixed pulley blocks;
second fixed pulley blocks fixed at either side of the arch leg assembly device, respectively, wherein the second flexible connection member is connected to the front wing plate of the first and second slide block support plate assembly via the second fixed pulley blocks.

4. The millimeter wave holographic scan imaging apparatus for inspecting a human body according to claim 3, wherein, the driving device comprising:
a reduction electrical motor;
a synchronous pulley coupled to an output shaft of the reduction electrical motor; and
a synchronous cog belt engaged with gear tooth of the synchronous pulley so as to rotate under action of the reduction electrical motor.

5. The millimeter wave holographic scan imaging apparatus for inspecting a human body according to claim 4, further comprising:
a pressing block for fixedly connecting the synchronous pulley to the saddle of one of the slide block support plate assemblies;
the driving device is configured to drive the one of the slide block support plate assemblies, thereby the other of the slide block support plate assemblies being driven via the first and second flexible connection members connected between two slide block support plate assemblies, to move up-down in opposite directions.

6. The millimeter wave holographic scan imaging apparatus for inspecting a human body according to claim 5, wherein,
the pressing block is configured to have an inward concave mating portion complementary in shape to an outward protruding tooth portion of the synchronous cog belt, the outward protruding tooth portion of the synchronous cog belt being depressed in the inward concave mating portion of the pressing block,
the saddle of the slide block support plate assembly is provided with an aperture, wherein, after the outward protruding tooth portion of the synchronous cog belt having been depressed in the inward concave mating portion of the pressing block, they are fixedly connected to the saddle of the slide block support plate assembly by a fastener.

7. The millimeter wave holographic scan imaging apparatus for inspecting a human body according to claim 6, further comprising:
an impact block mounted on the slide block support plate assembly, which moves up-down together with the slide block support plate assembly; and
a limit switch and a proximity switch disposed at either end position of the second guide track, the impact block and the proximity switch cooperate with each other to determine a zero position and a terminal position of the slide block support plate assembly and the impact block and the limit switch cooperate with each other to determine a limit position of the slide block support plate assembly.

8. The millimeter wave holographic scan imaging apparatus for inspecting a human body according to claim 1, wherein:
a plane, in which the first and the second millimeter wave transceiver devices are located, is configurable to be parallel to or subtend an angle with relation to a horizontal plane.

9. The millimeter wave holographic scan imaging apparatus for inspecting a human body according to claim 8, wherein:
the first and the second millimeter wave antenna arrays are configurable to be arranged in manner of strange line, serration line or curve line, so as to form the first and the second millimeter wave transceiver devices.

10. The millimeter wave holographic scan imaging apparatus for inspecting a human body according to claim 1, further comprising:
a data processing device configured to be wirelessly or wire coupled to the first and the second millimeter wave transceiver devices to receive scanning data from the first and the second millimeter wave transceiver devices and generate a millimeter wave holographic scan image; and
a display device configured to communicate with the data processing device, for receiving and displaying the millimeter wave holographic scan image from the data processing device.

11. The millimeter wave holographic scan imaging apparatus for inspecting a human body according to claim 10, further comprising:
a housing, which is configured to, together with the arch leg assembly, enclose a scanning space for performing scanning and imaging for an object to be inspected.

12. The millimeter wave holographic scan imaging apparatus for inspecting a human body according to claim 11, wherein,
the data processing device is located in a top space above the scanning space.

13. The millimeter wave holographic scan imaging apparatus for inspecting a human body according to claim 1, further comprising:
a control device configured to generate a control signal and transmit it to the driving device such that the driving device drives the first millimeter wave transceiver device and the second millimeter wave transceiver device to move.

14. The millimeter wave holographic scan imaging apparatus for inspecting a human body according to claim 1, wherein,
during the whole process of the first millimeter wave transceiver device and the second millimeter wave transceiver device together performing a scanning to an object to be inspected, the first millimeter wave signal and the second millimeter wave signal are configured to be transmitted in different frequency.

15. The millimeter wave holographic scan imaging apparatus for inspecting a human body according to claim 1, wherein,
during the whole process of the first millimeter wave transceiver device and the second millimeter wave transceiver device together performing a scanning to an object to be inspected, the first millimeter wave transceiver antenna array and the second millimeter wave transceiver antenna array are configured to be transmitted in different timing.

* * * * *